United States Patent [19]

Miller

[11] Patent Number: 5,749,519

[45] Date of Patent: May 12, 1998

[54] LIQUID AIR FRESHENER DISPENSER DEVICE WITH NONPOROUS WICKING MEANS

[75] Inventor: Eric J. Miller, Mt. Pleasant, Wis.

[73] Assignee: S. C. Johnson & Son, Inc., Racine, Wis.

[21] Appl. No.: 766,836

[22] Filed: Dec. 13, 1996

[51] Int. Cl.⁶ .................................................. A61L 9/00
[52] U.S. Cl. ................................................. 239/44; 239/34
[58] Field of Search .......................... 239/145, 34, 35, 239/44, 45, 49, 57, 51.5; 261/99, 110

[56] References Cited

U.S. PATENT DOCUMENTS

| | | | |
|---|---|---|---|
| 1,994,932 | 3/1935 | Vidal | 422/122 |
| 2,337,357 | 12/1943 | Stuewer | 239/44 X |
| 2,587,949 | 3/1952 | Zodtner | 401/223 |
| 2,597,195 | 5/1952 | Smith | 422/125 |
| 2,802,695 | 8/1957 | Johnson | 239/44 |
| 2,804,291 | 8/1957 | Hard af Segerstad | 239/44 X |
| 2,847,976 | 8/1958 | Spaulding | 401/292 |
| 3,278,175 | 10/1966 | Hirtz | 261/99 |
| 3,283,787 | 11/1966 | Davis | 239/34 X |
| 3,379,855 | 4/1968 | Forrester et al. | 239/44 X |
| 3,550,853 | 12/1970 | Gray | 239/44 |
| 3,724,962 | 4/1973 | Hernnring | 401/223 |
| 4,286,754 | 9/1981 | Jones | 239/6 |
| 4,413,779 | 11/1983 | Santini | 239/45 |
| 4,454,987 | 6/1984 | Mitchell | 239/6 |
| 4,768,676 | 9/1988 | Kaneko | 239/44 X |
| 4,913,350 | 4/1990 | Purzycki | 239/44 |
| 5,000,383 | 3/1991 | van der Heijden | 239/47 |
| 5,047,790 | 9/1991 | Cowger et al. | 347/87 |
| 5,121,881 | 6/1992 | Lembeck | 239/44 |

Primary Examiner—Lesley D. Morris

[57] ABSTRACT

This invention provides an air freshener dispenser device which consists of (a) a transparent container which has a content of liquid air freshener medium, (b) a transparent nonporous insert sleeve which is coextensive with the container sidewall interior surface, and (c) a container closure comprising a vapor-emanating surface mechanism, such as an absorbent matrix, which is in contact with the insert sleeve. The insert sleeve surface and the sidewall interior surface are in a capillary spacing proximity which provides an upward wicking passageway for transmission of the liquid air freshener medium to the vapor-emanating surface for evaporation into the atmosphere.

12 Claims, 2 Drawing Sheets

U.S. Patent    May 12, 1998    Sheet 2 of 2    5,749,519
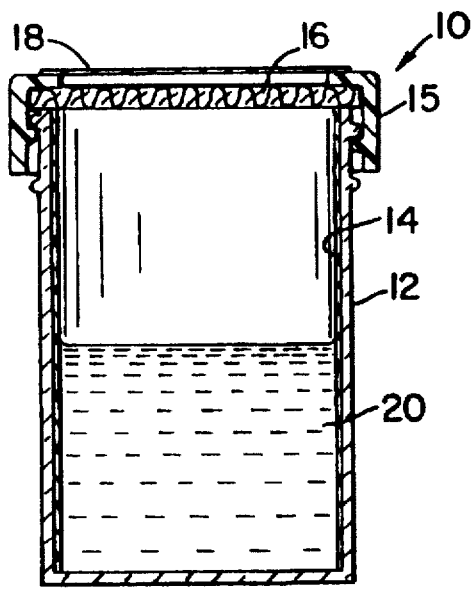
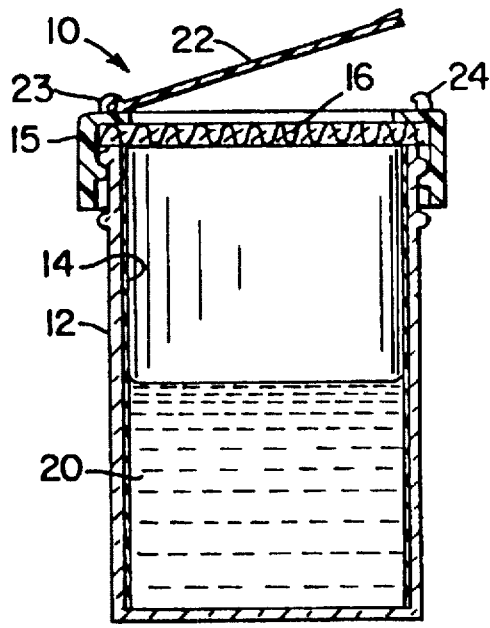
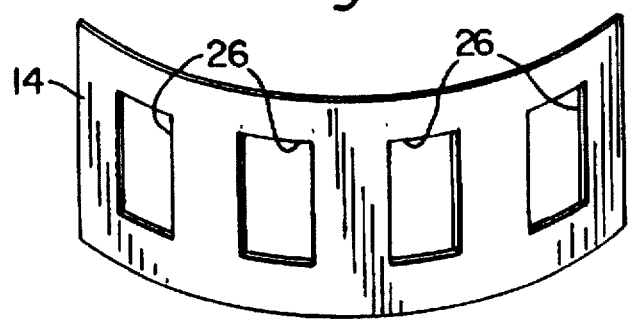
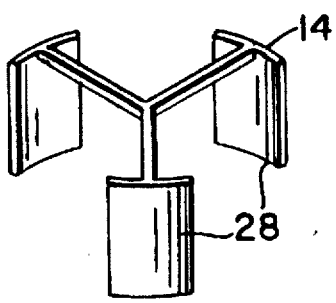
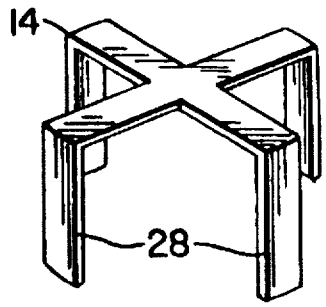

5,749,519

LIQUID AIR FRESHENER DISPENSER DEVICE WITH NONPOROUS WICKING MEANS

BACKGROUND OF THE INVENTION

This invention generally relates to dispensers of vaporizable media. More specifically, this invention relates to a device for dispensing a fragrance or deodorant in the form of a vapor for air freshening in an enclosed environment.

The need for effectively combating airborne malodors in homes and enclosed public buildings, by odor masking or destruction, is well established. Various kinds of vapor-dispensing devices have been employed for this purpose. The most common of such devices is the aerosol container which propels minute droplets of an air freshener composition into the air. Another common type of dispensing device is a dish containing or supporting a body of gelatinous matter which when it dries and shrinks releases a vaporized air-treating composition into the atmosphere. Other products such as deodorant blocks are also used for dispensing air-treating vapors into the atmosphere by evaporation. Another group of vapor-dispensing devices utilizes a carrier material such as paperboard impregnated or coated with a vaporizable composition.

A number of recent developments include a liquid air-treating composition in an enclosure, all or part of which is formed of a polymeric film through which the air-treating composition can migrate to be released as a vapor at an outer surface. Use of this type of permeable polymeric membrane controls the dispensing of air-treating vapors and tends to eliminate great variations in the rate of dispensing over the life of the product. Wicking devices are well known for dispensing volatile liquids into the atmosphere, such as fragrance, deodorant, disinfectant or insecticide active agent.

A typical wicking device utilizes a combination of a wick and emanating region to dispense a volatile liquid from a liquid reservoir. Wicking devices are described in U.S. Pat. Nos. 1,994,932; 2,597,195; 2,802,695; 2,804,291; 3,550,853; 4,286,754; 4,413,779; 4,454,987; 4,913,350; and 5,000,383; incorporated by reference.

Of special interest with respect to the present invention are wicking dispenser devices in which the wicking action is promoted by a nonporous wick structure. This type of device is described in U.S. Pat. Nos. 2,847,976; 3,283,787; 4,913,350; and 5,121,881; incorporated by reference.

Some air freshener dispensers are expensive to manufacture.

Other air freshener dispensers are inexpensive to produce, but tend to have inferior construction and functionality.

There remains a need for a well-constructed air freshener dispenser device which can be mass-produced economically and which can deliver a vapor medium at a controlled uniform rate over an extended period of time.

Accordingly, it is an object of this invention to provide an improved air freshener dispenser device for delivering an odorant and/or deodorant vapor in an enclosed environment.

It is another object of this invention to provide an air freshener dispenser device with a primary structure which is a plastic assembly that can be produced economically by a thermoforming means.

It is another object of this invention to provide an air freshener dispenser device which has a novel assembly of vapor-emanating surface and wicking means.

It is a further object of this invention to provide an air freshener dispenser device in which a liquid air freshener is transported from an enclosed reservoir to a vapor-emanating surface by capillary action with a nonporous wick structure.

Other objects and advantages of the present invention shall become apparent from the accompanying description and drawings.

SUMMARY OF THE INVENTION

One or more objects of the present invention are accomplished by the provision of an air freshener dispenser device comprising:

(a) a sheer sidewall container which encloses a reservoir of liquid air freshener medium;

(b) a nonporous insert sleeve which is in coextensive proximity to the container sidewall interior surface, and which is in contact with the air freshener medium; and (c) a container closure comprising a vapor-emanating surface means which is in contact with the interior insert sleeve; wherein the sidewall interior surface and insert sleeve surface are in a capillary spacing proximity which provides a wicking means for transmission of the liquid air freshener medium from the enclosed reservoir to the vapor-emanating surface for evaporation into the atmosphere.

DESCRIPTION OF THE DRAWINGS

FIG. 4 is a cross-sectional side view of a FIG. 2 invention device.

FIG. 5 is a cross-sectional side view of an invention air freshener dispenser device with a hinged cap section.

FIG. 6 is a prospective view of a flexible plastic insert sleeve in an uncoiled configuration.

FIG. 7 and FIG. 8 are prospective views illustrating alternative forms of semi-rigid thermoplastic insert sleeves for an invention air freshener dispenser device.

DESCRIPTION OF THE PREFERRED EMBODIMENTS

Figure 1:
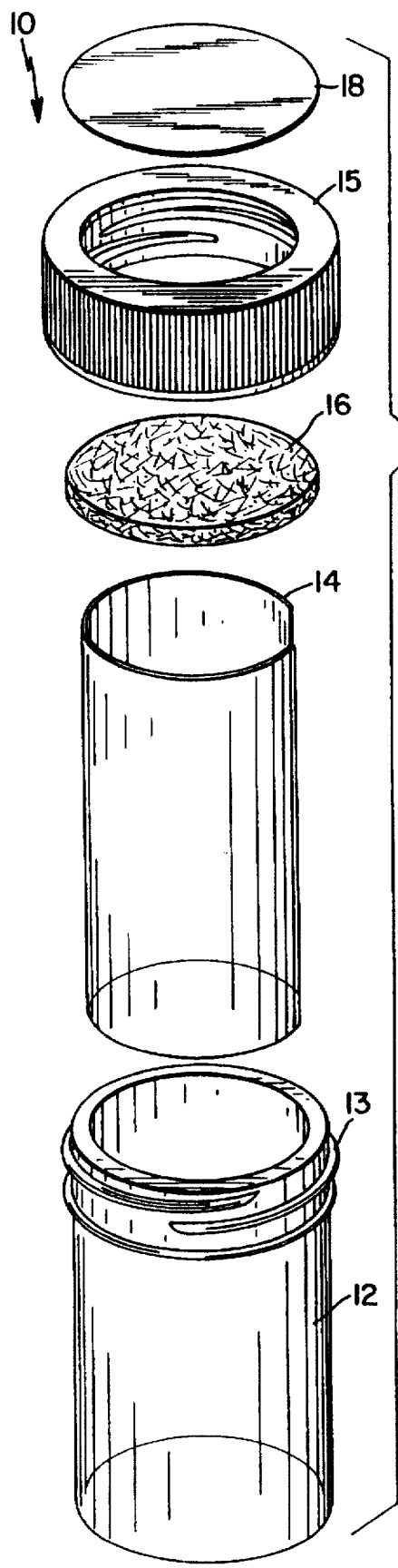
FIG. 1 is a composite prospective view of an invention air freshener dispenser device.

FIG. 1 illustrates an exploded view of present invention air freshener device 10.

Air freshener device 10 as illustrated is composed of transparent semi-rigid thermoplastic container 12 which is cylindrical, and which has threads 13 for engagement with closure cap 15. Closure cap 15 has an internally encompassed vapor-emanating surface means, absorbent matrix 16, which initially is covered with peelable seal means 18.

Nonporous insert sleeve 14 as illustrated is a transparent flexible film which typically has a coloration.

Figure 2:
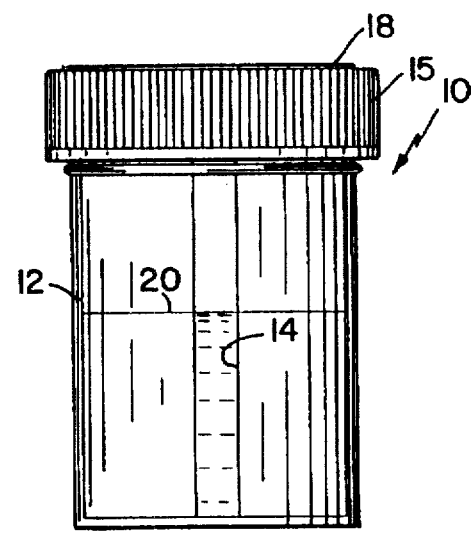
FIG. 2 is a side elevation view of a FIG. 1 invention device in assembled form.

FIG. 2 is a side elevation of air freshener device 10, which is in assembled form prior to usage. Air freshener medium 20 is in contact with insert sleeve 14, and is visible in the interior reservoir of container 12.

Figure 3:
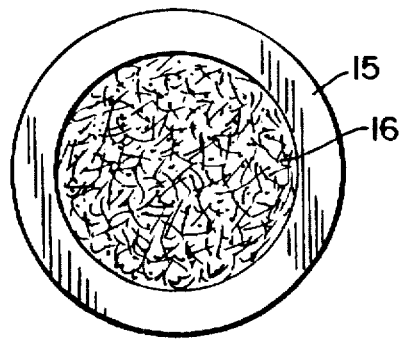
FIG. 3 is a top elevation view of an invention device cap with an absorbent matrix type of vapor-emanating surface exposed to the atmosphere.

FIG. 3 is a top elevation view of closure cap 15, after removal of seal means 18. The illustrated vapor-emanating surface means, absorbent matrix 16, is exposed to the atmosphere, and it dispenses air freshener medium 20 into the atmosphere in vapor form. Absorbent matrix 16 is in contact with the upper peripheral edge of insert sleeve 14.

FIG. 4 is a cross-sectional side view of FIG. 2 air freshener device 10, which illustrates the contacting relationship of insert sleeve 14 with air freshener medium 20 and absorbent matrix 16. The surface of insert sleeve 14 and the interior surface of container 12 are in a capillary spacing proximity which provides an upward wicking pressure for transmission of air freshener medium 20 from the interior reservoir to absorbent matrix 16 for evaporation into the atmosphere. Nominally the capillary spacing proximity is in the range between about 0.1–2 millimeters, and is in a hydrodynamic relationship with the surface tension properties of liquid air freshener medium 20.

FIG. 5 is a cross-sectional side view of air freshener device 10.

As illustrated, cap section 22 is rotatably connected to closure cap 15 by hinge 23. Cap section 22 in a closed position is secured by snap-in means 24.

Closure cap 15 can be a thermoformed structure of a polymer such as high density polyethylene or polypropylene.

FIG. 6 illustrates a prospective view of insert sleeve 14 in the form of a transparent flexible film of a thermoplastic polymer such as polyvinyl, polyester, polyamide or polysiloxane resins. Open spaces 26 can be any number or design, with the proviso that there is at least a sufficient capillary pathway for transmission of air freshener medium 20 from the reservoir to absorbent matrix 16.

FIG. 7 and FIG. 8 are prospective views illustrating optional structural configurations for insert sleeve 14. As illustrated in FIG. 7 and FIG. 8, insert sleeve 14 can be a nonporous semi-rigid thermoformed structure of a thermoplastic polymer such as polypropylene or polystyrene which is impervious to air freshener medium 20.

In FIG. 7 and FIG. 8, extended leg sections 28 of insert sleeve 14 are adapted to provide a capillary spacing proximity with the interior sidewall surface of container 12 in air freshener device 10.

Insert sleeve 14 preferably provides a capillary spacing proximity with at least about one percent of the interior sidewall periphery of container 12. A typical air freshener device 10 has a container with an interior sidewall periphery size between about 5–25 centimeters, and insert sleeve 14 provides a capillary spacing proximity with at least about 0.5 millimeter of the sidewall periphery.

Container 12 normally is constructed by either injection or thermoform molding of a thermoplastic polymer such as polyethylene, polypropylene, polystyrene, polyvinyl acetate, polyamide, polymethacrylate, and the like. Container 12 can be an annular-shaped structure with a vertical or slanted sidewall, or it can be a square or rectangular structure. A container sidewall also can have a concave curvature. Container 12 can be any convenient design, with the proviso that insert sleeve 14 provides at least an effective degree of capillary spacing proximity with the sidewall interior surface of container 12, and is in interacting contact with both air freshener medium 20 and absorbent matrix 16.

Closure cap 15 is secured to container 12 by a connecting means, such as a screw-on or snap-on feature. Closure cap 15 also can be permanently secured by adhesive or weld means. Closure cap 15 encompasses internally disposed absorbent matrix 16. During usage of air freshener device 10, the bottom of absorbent matrix 16 is in contact with insert sleeve 14, and the top of absorbent matrix 16 is exposed to the atmosphere for the transmission of air freshener 20 in vapor form.

The vapor-emanating surface means of air freshener device 10, e.g., absorbent matrix 16, can be an organic or inorganic liquid-permeable structure, such as a thermoplastic, thermoset, cellulosic or ceramic composition. The dimensions of absorbent matrix 16 can frictionally secure the structure within closure cap 15.

Air freshener medium 20 in FIG. 2 can be any air treating material which can be wicked up to absorbent matrix 16 by capillary action, and dispersed into the atmosphere in vapor form. Typically air freshener medium 20 is a fragrance or a deodorant formulation in liquid form.

Air freshener medium 20 preferably is a liquid fragrance comprising one or more volatile organic compounds which are available from perfumery suppliers such as Firmenich Inc., Takasago Inc., Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

Air freshener medium 20 also can be a liquid formulation containing a volatile pesticide such as p-dichlorobenzene, or a therapeutic agent such as menthol.

Air freshener device 10 preferably is constructed of transparent or translucent materials, such that air freshener medium 20 is visible during usage for an indication of the liquid level in the interior reservoir.

A present invention air freshener device can be produced in high volume from relatively inexpensive plastic materials. After usage, the device qualifies for disposal as a non-hazardous solid waste.

What is claimed is:

1. An air freshener dispenser device comprising:
    (a) a sheer sidewall container which encloses a reservoir of liquid air freshener medium;
    (b) a nonporous insert sleeve which is in coextensive proximity to the container sidewall interior surface, and which is in contact with the air freshener medium; and
    (c) a container closure comprising a vapor-emanating surface means which is in contact with the interior insert sleeve; wherein the sidewall interior surface and insert sleeve surface are in a capillary spacing proximity which provides a wicking means for transmission of the liquid air freshener medium from the enclosed reservoir to the vapor-emanating surface for evaporation into the atmosphere.

2. A dispenser device in accordance with claim 1 wherein the container has an annular-shaped structure comprising a transparent thermoplastic composition.

3. A dispenser device in accordance with claim 1 wherein the air freshener medium is a liquid fragrance composition.

4. A dispenser device in accordance with claim 1 wherein the air freshener medium is a liquid pesticide composition.

5. A dispenser device in accordance with claim 1 wherein the air freshener medium is a liquid therapeutic composition.

6. A dispenser device in accordance with claim 1 wherein the insert sleeve is a flexible film comprising a thermoplastic polymer selected from the group consisting of polyvinyl, polyester, polyamide and polysiloxane resins.

7. A dispenser device in accordance with claim 1 wherein the insert sleeve is a flexible glass sheet.

8. A dispenser device in accordance with claim 1 wherein the insert sleeve provides a capillary spacing proximity with at least about one percent of the interior sidewall periphery of the container.

9. A dispenser device in accordance with claim 1 wherein the container has an interior sidewall periphery size between about 5–25 centimeters, and the insert sleeve provides a capillary spacing proximity with at least about 0.5 millimeter of the sidewall periphery.

10. A dispenser device in accordance with claim 1 wherein the vapor-emanating surface means is an absorbent matrix comprising a thermoplastic, thermoset, cellulosic or ceramic composition.

11. A dispenser device in accordance with claim 1 wherein the vapor-emanating surface means is integral with a cap-type closure, and the vapor-emanating surface is isolated from the exterior environment by a removable seal means.

12. A dispenser device in accordance with claim 1 wherein the vapor-emanating surface means is integral with a cap-type closure, and the vapor-emanating surface is isolated from the exterior environment by a hinged seal means.

\* \* \* \* \*